United States Patent [19]

Cornell et al.

[11] 4,372,336
[45] Feb. 8, 1983

[54] CHEST DRAINAGE UNIT

[75] Inventors: William D. Cornell, Ballwin; Ronald Crouther, Manchester; Howard P. Dyer, Webster Groves; Alan B. Ranford, Des Peres, all of Mo.

[73] Assignee: Sherwood Medical Industries, Inc., St. Louis, Mo.

[21] Appl. No.: 160,447

[22] Filed: Jun. 17, 1980

[51] Int. Cl.³ .............................................. A61M 1/00
[52] U.S. Cl. ...................................... 137/205; 128/276
[58] Field of Search ................. 137/205; 128/276, 277

[56] References Cited

U.S. PATENT DOCUMENTS

| | | |
|---|---|---|
| 3,052,064 | 9/1962 | Kaeser .......................... 251/61.1 X |
| 3,363,626 | 1/1968 | Bidwell .......................... 137/205 X |
| 3,610,478 | 10/1971 | Johnston ........................ 137/212 X |
| 3,945,392 | 3/1976 | Deaton ............................... 137/205 |
| 4,261,362 | 4/1981 | Kurtz et al. ......................... 128/276 |
| 4,275,997 | 6/1981 | Woodring ..................... 251/61.1 X |

FOREIGN PATENT DOCUMENTS 957118 5/1964 United Kingdom ......... 137/DIG. 8

*Primary Examiner*—Alan Cohan
*Attorney, Agent, or Firm*—Paul L. Gardner

[57] ABSTRACT

An improved, four-chamber chest drainage system include (1) a collection chamber for collecting blood and other liquids to be drained from the pleural cavity of a patient, (2) an underwater seal chamber for preventing contamination of the patient's pleural cavity by atmospheric air, (3) a manometer chamber for accurately indicating the negative pressure in the patient's pleural cavity, and (4) a suction control chamber for regulating the amount of negative pressure (or suction) applied to the patient's pleural cavity. The suction control chamber has a flexible diaphragm adapted to flex in response to increased negativity above a predetermined level to block the opening to the suction source until the negativity returns to the predetermined level. A combination vent valve-and-filter assembly permits ready venting of the collection chamber to filtered atmospheric air.

2 Claims, 29 Drawing Figures

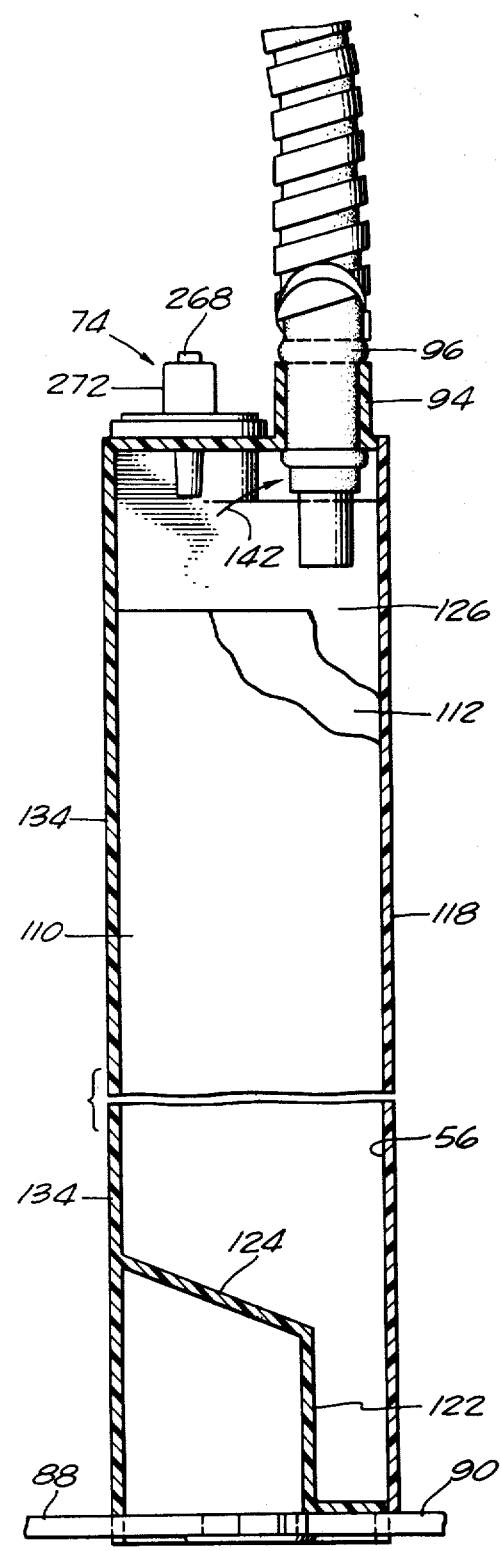
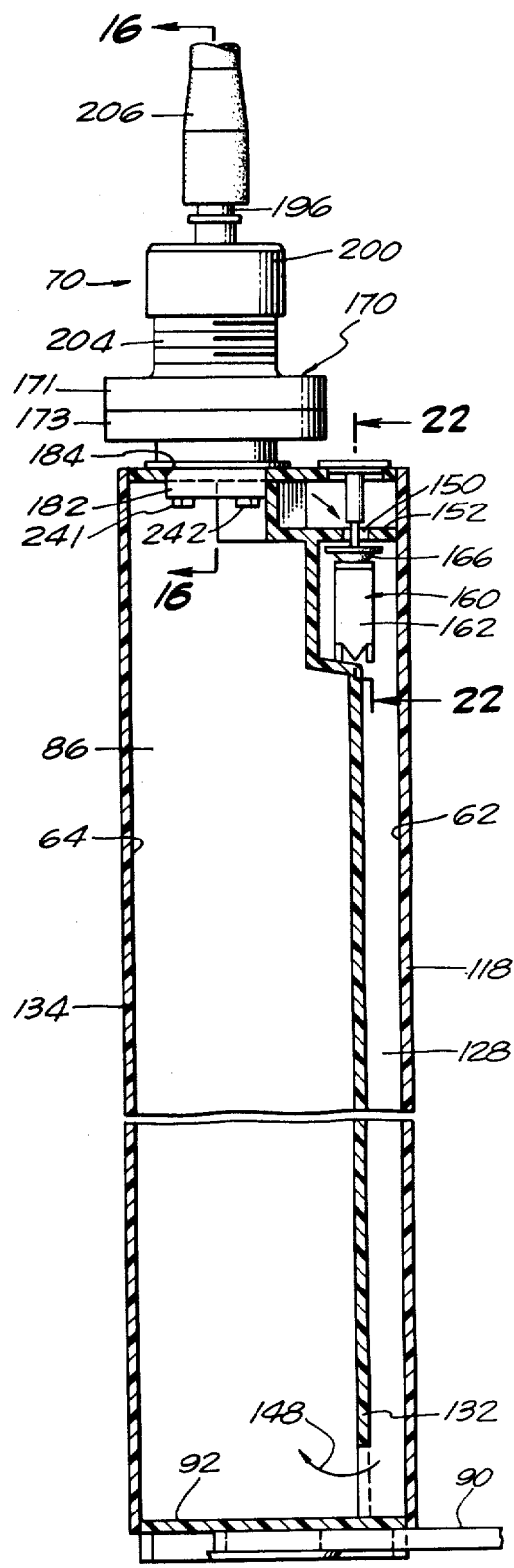
FIG. 4
FIG. 5

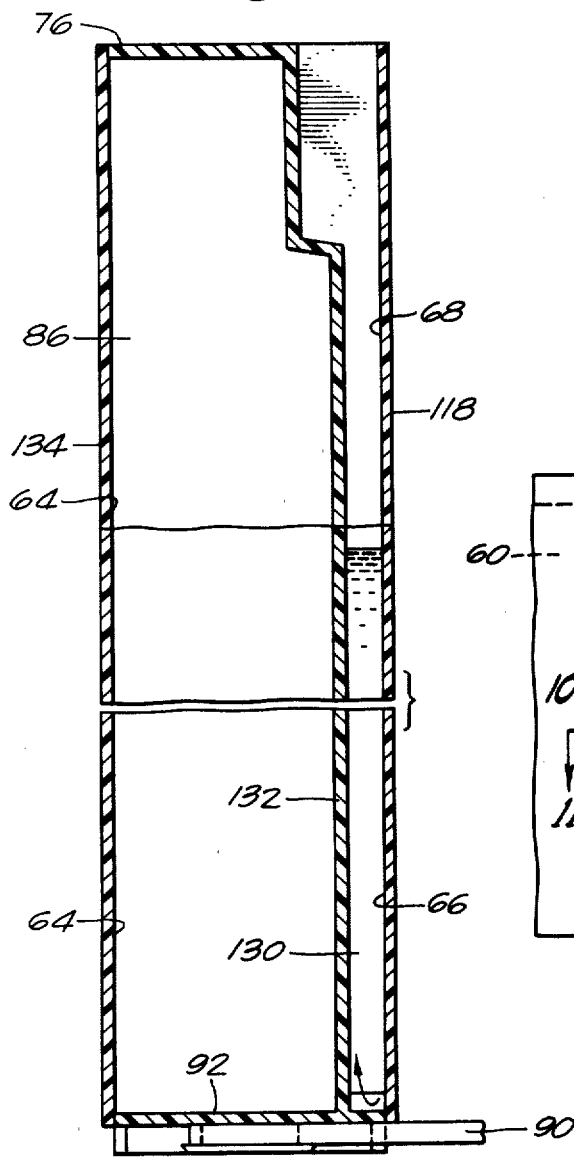
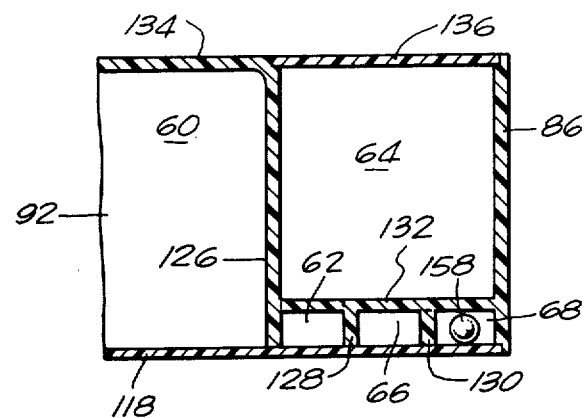
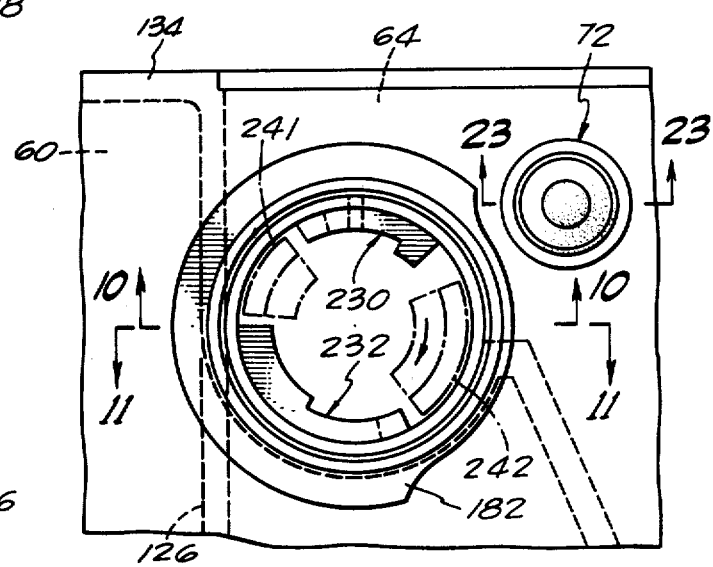
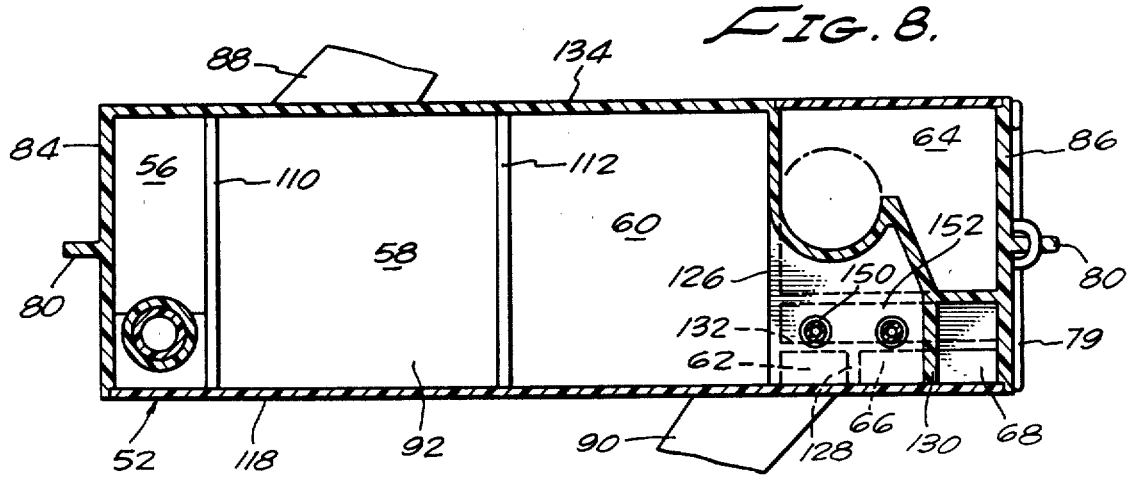

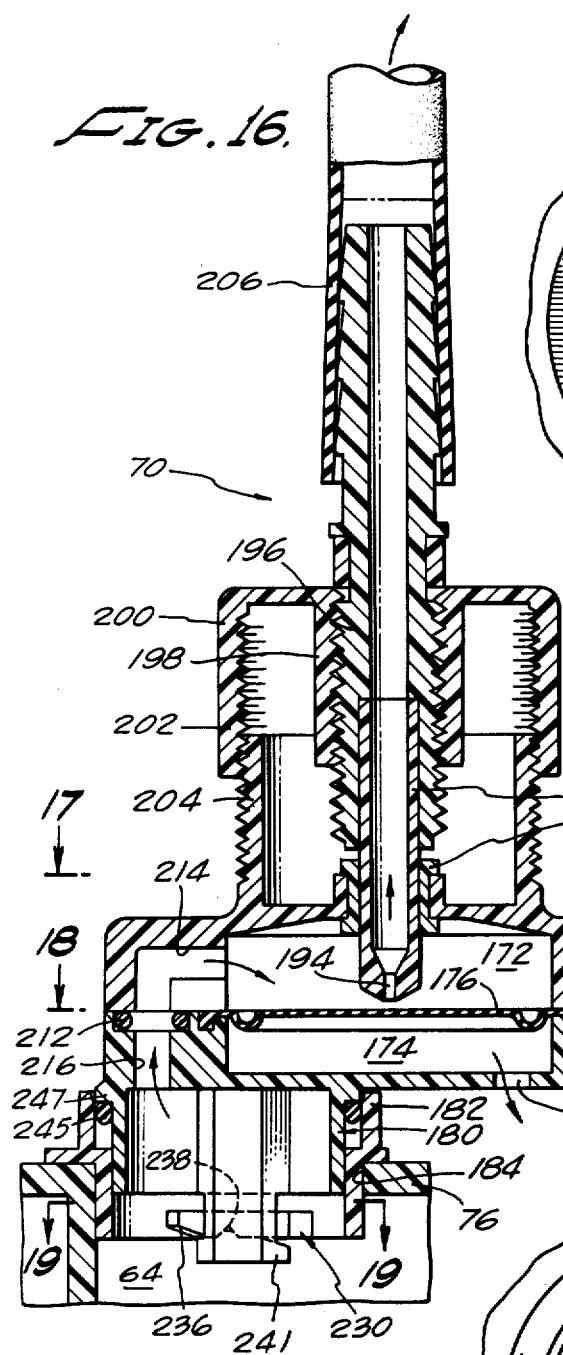
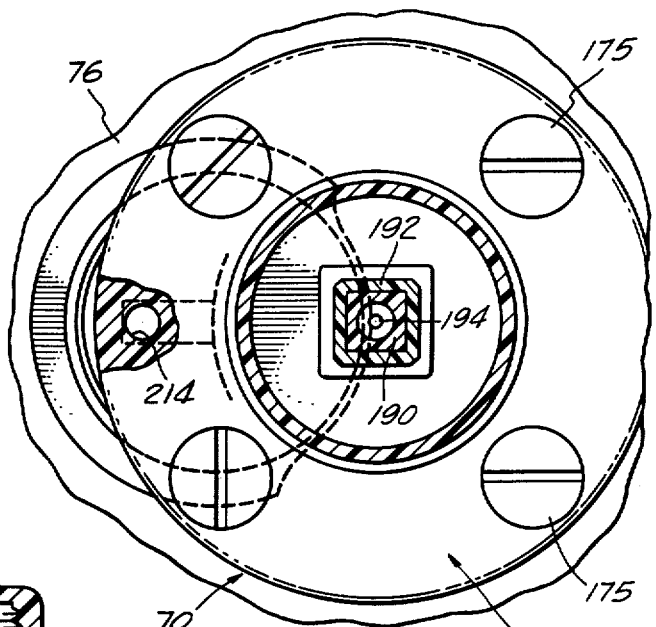
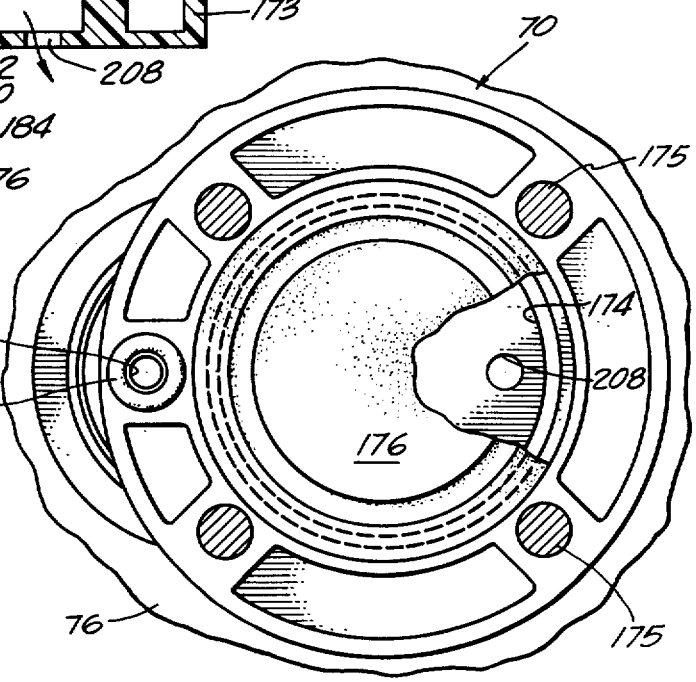

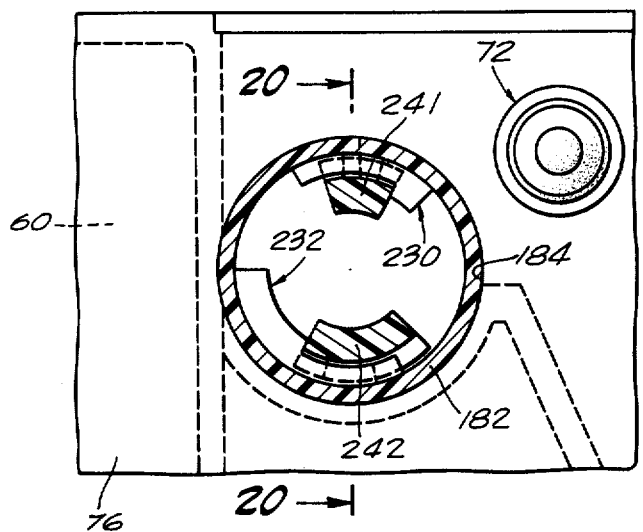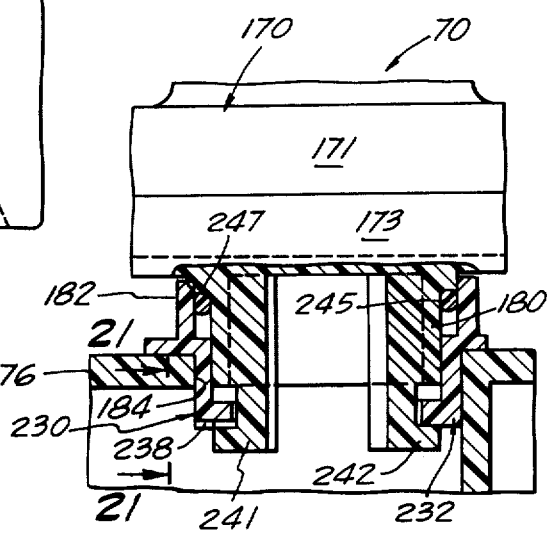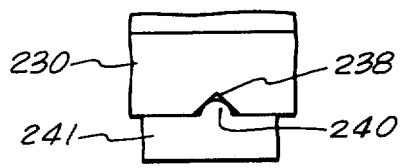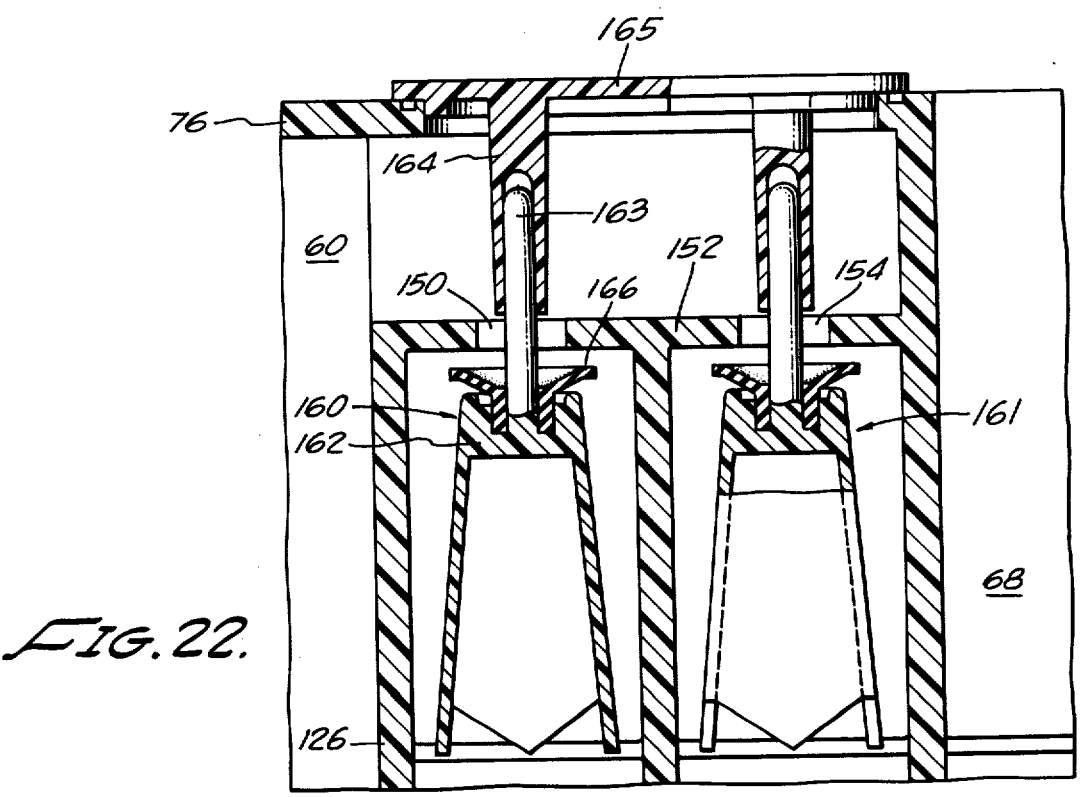

CHEST DRAINAGE UNIT

FIELD OF THE INVENTION

The present invention relates to chest drainage systems, sometimes referred to as underwater drainage apparatus, for suctioning gases and liquids from the chest cavities of patients (e.g., who have undergone thoracic surgery).

BACKGROUND OF THE INVENTION

In recent years two types of chest drainage systems have been growing in popularity among physicians and hospital personnel.

One type, sometimes referred to as a "three-bottle" type, is illustrated in U.S. Pat. No. 3,363,626, issued Jan. 16, 1968. The "three-bottle" unit derives its name from the fact that it incorporates three chambers which perform the same functions as the three bottles of the so-called "classic three-bottle system" which has been used since the 1940's. (The "classic three-bottle system" is illustrated and described, for example, in an article entitled "A Comparative Study of the Physiology and Physics of Pleural Drainage Systems" by Enerson and McIntyre, particularly at page 42, July 1966 issue of *The Journal of Thoracic and Cardiovascular Surgery*, Vol. 52, No. 1, and in an article entitled "The New Underwater Suction Drainage Unit," by Engelsher, particularly at page 197, February 1967 issue of *Surgery*, and also in the book entitled *Thoracic Surgery*, Second Edition, by Sweet, particularly at page 55.)

The three chambers of the so-called "three-bottle system" comprise (1) a collection chamber for collecting blood and other liquids suctioned from the patient's pleural cavity, (2) an underwater seal chamber having a liquid seal which acts as a one-way valve for passing gases from the patient's pleural cavity to the atmosphere, and (3) a suction control chamber for limiting the maximum suction (or negative pressure) applied to the patient's pleural cavity.

The second type of chest drainage system which has become popular in recent years has come to be known as the "four-bottle system." The "four-bottle system" is illustrated and described, for example, in U.S. Pat. No. 3,757,783 issued Sept. 11, 1973 to Alley, and in U.S. Pat. No. 3,783,870 issued Jan. 8, 1974 to Schachet. This system was designed to overcome some of the deficiencies associated with the "three-bottle unit," such as the dangers associated with unintentional "closing" of the system and also the difficulty in reading the level of suction due to bubbling in the suction control/manometer chamber.

The "four-bottle system" includes the three chambers of the "three-bottle unit," and adds a fourth chamber, called a safety seal/manometer chamber, which provides an accurate indicia of the level of suction being applied to the cavity to be drained, and also acts as a one-way valve to vent excess pressure created, for example, by failure of the system in a "closed" state.

The "four-bottle system" of the prior art (e.g., U.S. Pat. Nos. 3,757,783 and 3,783,870) did not overcome all of the deficiencies of the "three-bottle unit." More specifically, the suction control chamber in the "four-bottle system" remains noisy due to bubbling of atmospheric air through the liquid therein; and the system is somewhat bulky. With increased awareness of the anxiety-provoking nature of noise in the hospital environment (see, e.g., "The Perceptual World of the ICU," Gowan, March–April, 1979 issue of *Heart and Lung*, Vol. 8, No. 2, pp. 340–344) there is a substantial need and demand for a quiet chest drainage system.

Another disadvantage of the prior art chest drainage systems arises when it becomes necessary to vent the collection chamber to atmosphere to reduce the negativity or suction therein. The prior art method of venting comprises the insertion of a filtered needle into the latex tube which connects the patient's chest cavity to the collection chamber, a somewhat cumbersome procedure.

OBJECTS OF THE INVENTION

Among the objects of the present invention is the provision of a chest drainage unit which is smaller, more convenient, quiet and less expensive than the present "four-bottle system," but which retains all of the functional advantages thereof.

Another object of the present invention is the provision of means for quickly, conveniently, and safely venting the collection chamber of a chest drainage unit to filtered atmospheric air without having to insert a filtered needle into the latex tube which connects the unit to a thoracic catheter which, in turn, is connected to the patient's chest cavity to be drained.

SUMMARY OF THE INVENTION

The foregoing and other objects have been realized by the chest drainage system of the present invention which employs a suction control chamber without liquid, hence without noise-producing bubbling. The suction control chamber of the present invention employs a flexible diaphragm which blocks communication between the patient and the suction source when the level of suction exceeds a predetermined value.

The system of the present invention includes, in addition to an improved suction control technique, a collection chamber in series with an underwater seal chamber and a manometer chamber, the underwater seal chamber and the manometer chamber being in parallel with one another.

The present invention further includes a combination vent valve-and-filter assembly which permits venting of negative pressure (i.e., suction) in the collection chamber by a simple pushbutton step to admit filtered air to the collection chamber.

BRIEF DESCRIPTION OF THE DRAWINGS

FIG. 4 is a sectional, side elevation view of the unit shown in FIGS. 1-3, taken along the plane 4—4 of FIG. 3 and looking in the direction of the arrows.

FIG. 5 is a sectional, side elevation view taken along the plane 5—5 of FIG. 3 and looking in the direction of the arrows.

FIG. 6 is a sectional, side elevation view taken along the plane 6—6 of FIG. 3 and looking in the direction of the arrows.

FIG. 7 is a partial, sectional, top view taken along the plane 7—7 of FIG. 3 and looking in the direction of the arrows.

FIG. 8 is a sectional, top view taken along the plane 8—8 of FIG. 3 and looking in the direction of the arrows.

FIG. 9 is a partial, enlarged, top view illustrating the opening in the top wall of the unit shown in FIGS. 1-8, which is adapted to receive the suction regulator of the unit.

FIG. 16 is a cross-sectional elevation view of the suction regulator taken along the plane 16—16 of FIG. 5 and looking in the direction of the arrows.

FIG. 17 is a cross-sectional top view taken along the plane 17—17 of FIG. 16 and looking in the direction of the arrows.

FIG. 18 is a cross-sectional top view taken along the plane 18—18 of FIG. 16 and looking in the direction of the arrows.

FIG. 19 is a cross-sectional top view taken along the plane 19—19 of FIG. 16 and looking in the direction of the arrows.

FIG. 20 is a cross-sectional elevation view taken along the plane 20—20 of FIG. 19 and looking in the direction of the arrows.

FIG. 21 is a partial, elevation view, looking from the vantage point of the plane 21—21 of FIG. 20, in the direction of the arrows, showing the locking detent for holding the suction regulator in place on the top wall of the casing.

FIG. 22 is a sectional, front elevation view taken along the plane 22—22 of FIG. 5 and looking in the direction of the arrows, illustrating the overflow-prevention float valve structure in the upper portion of one of the compartments in the manometer chamber and the adjacent compartment of the underwater seal chamber of the unit.

DESCRIPTION OF PREFERRED EMBODIMENT

Figure 1:
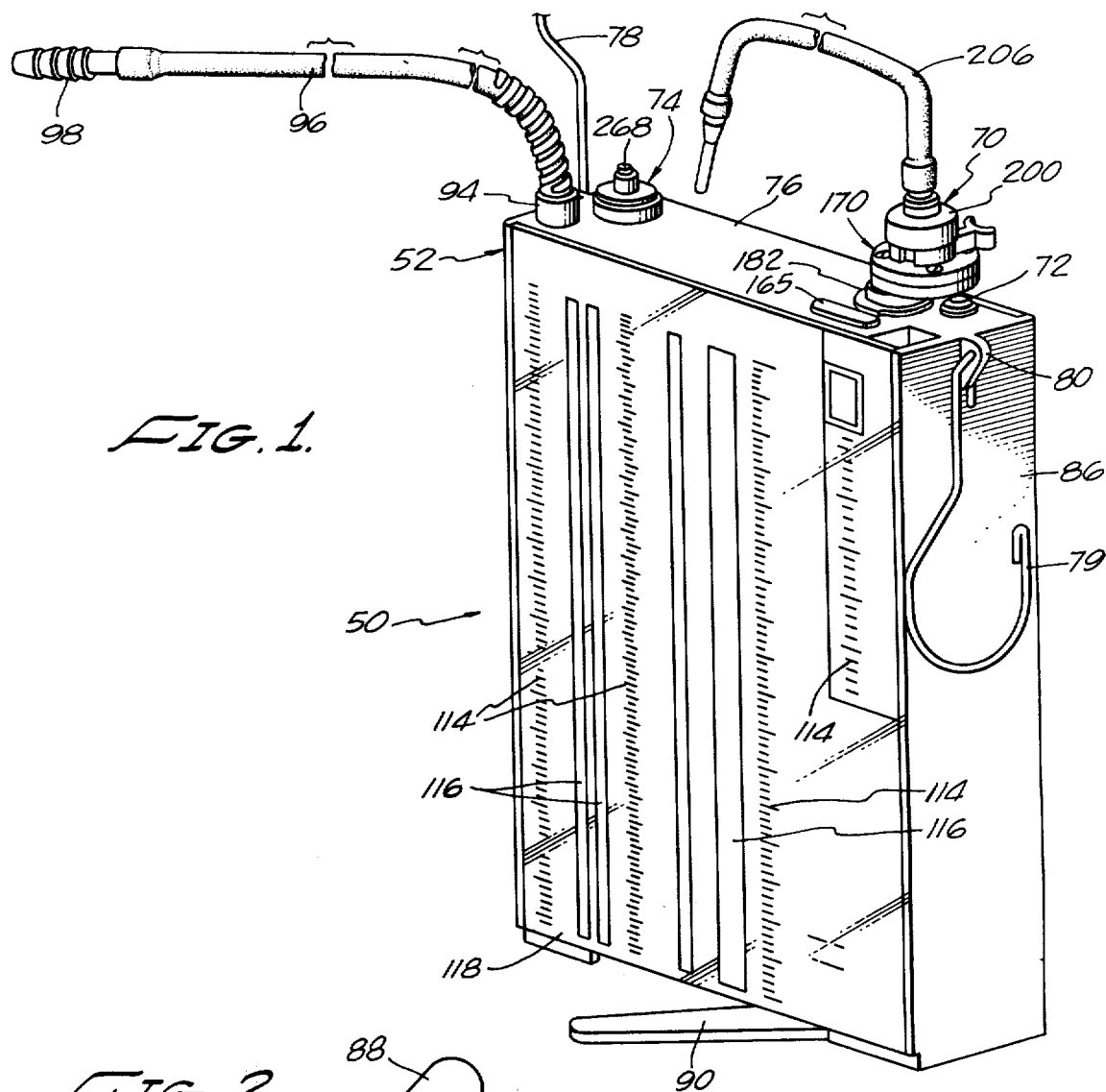
FIG. 1 is an isometric view of an improved chest drainage unit constructed in accordance with the teachings of the present invention.
Figure 2:
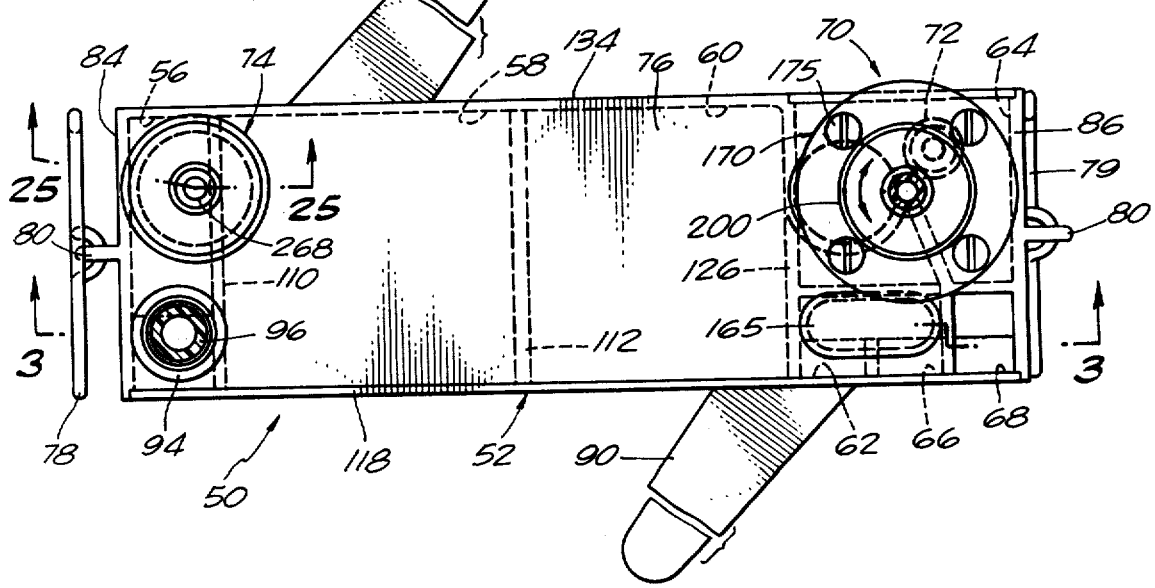
FIG. 2 is a top view of the unit shown in FIG. 1.
Figure 3:
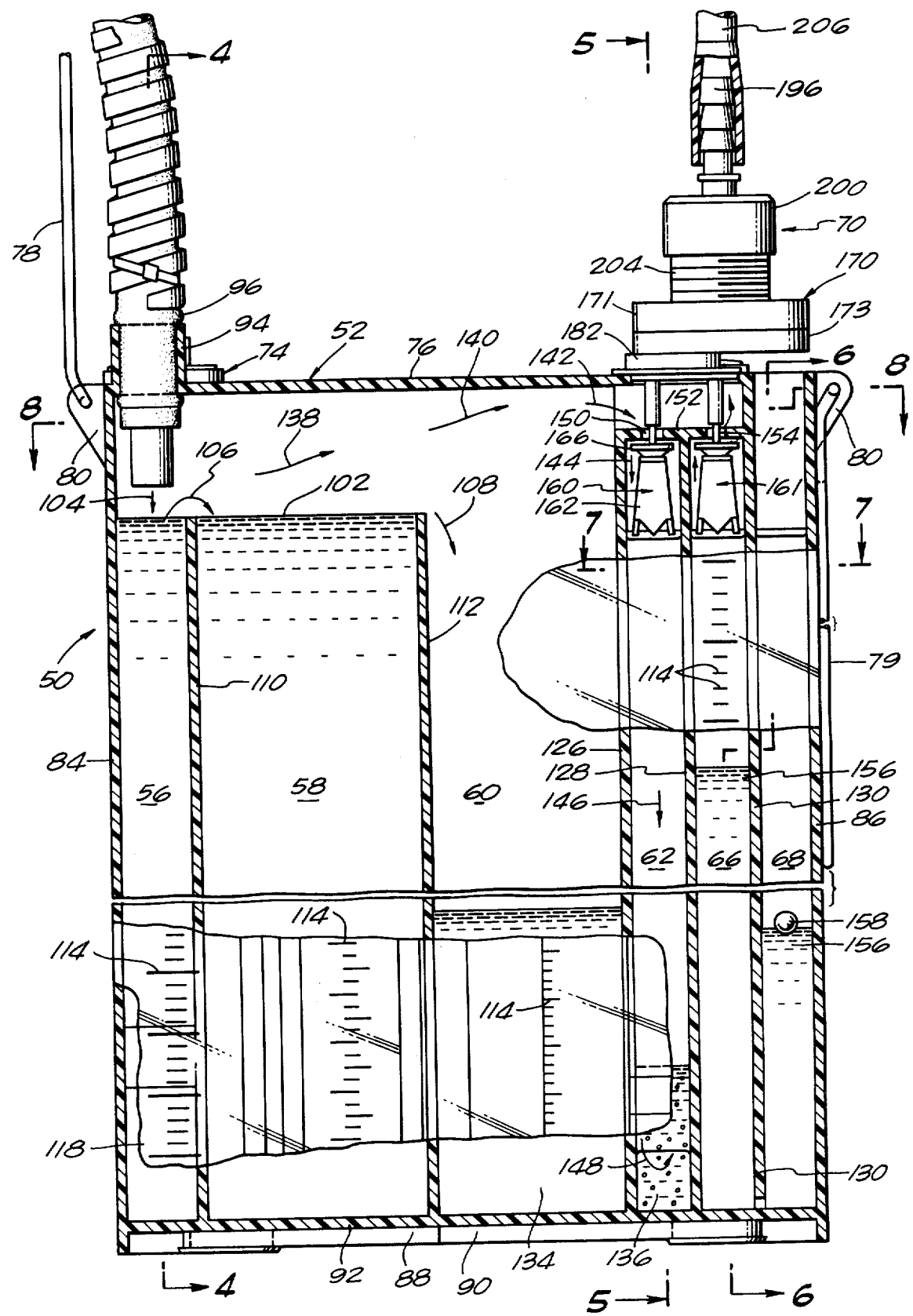
FIG. 3 is a sectional, front elevation view of the unit shown in FIGS. 1 and 2, taken along the plane 3—3 of FIG. 2 and looking in the direction of the arrows.
Figure 10:
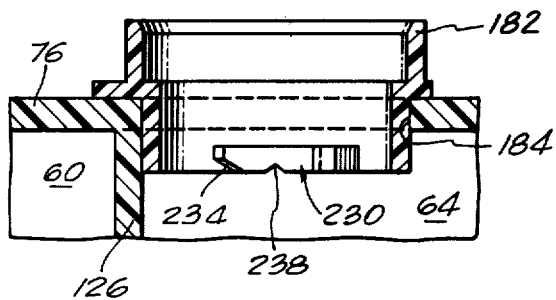
FIG. 10 is a partial, sectional, side elevation view taken along the line 10—10 of FIG. 9 and looking in the direction of the arrows.
Figure 11:
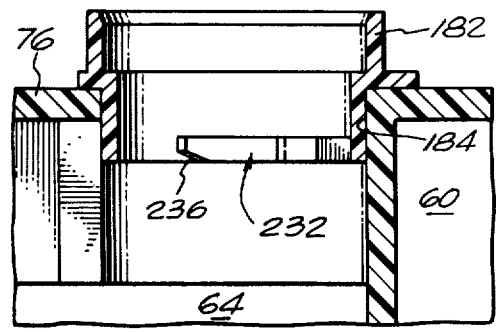
FIG. 11 is a partial, sectional, side elevation view taken along the plane 11—11 of FIG. 9 and looking in the direction of the arrows.
Figure 12:
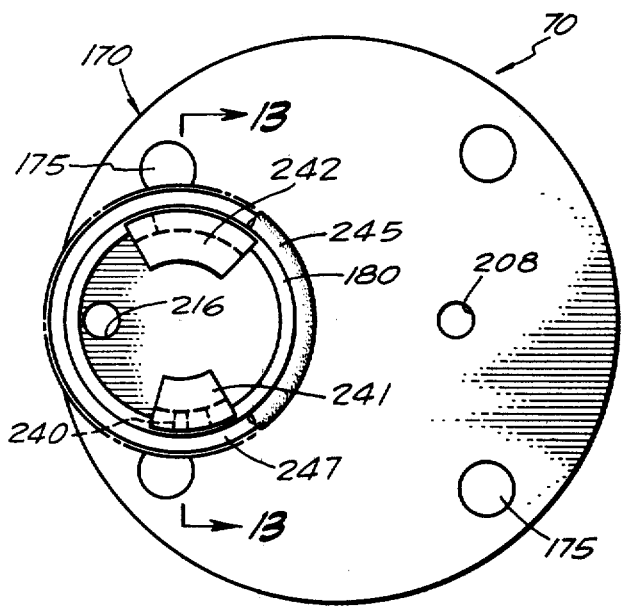
FIG. 12 is a bottom view of the suction regulator of the preferred embodiment of the improved chest drainage unit of the present invention.
Figure 13:
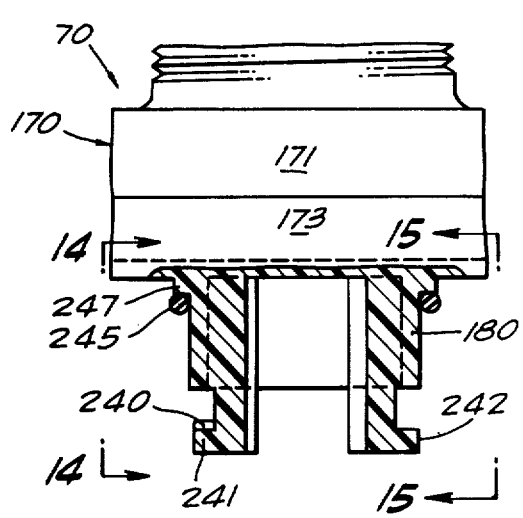
FIG. 13 is a partial, sectional, side elevation view taken along the plane 13—13 of FIG. 12 and looking in the direction of the arrows.

Referring to FIGS. 1, 2 and 3, the chest drainage system 50 constituting the preferred embodiment illustrated in the drawings comprises a casing 52 having a top wall 76, a bottom wall 92, front and rear walls 118 and 134, respectively, and end walls 84 and 86. Interior partitions 110, 112, 126, 128 and 130 (see FIG. 3), all parallel to end walls 84 and 86, and a partition 132 (FIG. 7), which is parallel to front and rear walls 118, 134, divide the interior of casing 52 into a plurality of compartments, 56, 58, 60, 62, 64, 66 and 68.

Compartments 56, 58 and 60 constitute the collection chamber of the system; compartments 62 and 64 (best shown in FIGS. 3 and 7) constitute the underwater seal chamber; and compartments 66 and 68 comprise the manometer chamber of the system 50.

The system 50 further comprises a suction regulator 70, a pop-off type safety valve 72 and a combination vent valve-and-filter unit 74, all mounted in the top wall 76 of casing 52.

The chest drainage system 50 may be conveniently hung on the patient's bed by means of hangers 78, 79 which have their interior ends rotatably mounted in ears 80, 80 at the top of end walls 84 and 86.

Alternatively, the system 50 may stand on the floor with the support of swing-out legs 88, 90 pivotably mounted on the bottom wall 92 of the casing 52.

As best shown in FIG. 1, gradations 114 and writing surface material 116 are provided on the front wall 118 of the casing 52. The gradations provide ready indicia of the levels of liquid in the various compartments; and the writing surface material facilitates the marking of the level of liquid (e.g., blood, etc.) collected in the compartments 56, 58 and 60, which constitute the collection chamber, at selected time intervals.

As best shown in FIGS. 1 and 3, the top wall 76 of the casing 52 is provided with a fitting 94 for receiving the outer end of a latex tube 96. The other end of the latex tube 96 is provided with an adapter 98 designed for connection to a thoracic catheter (not shown) leading to the patient's chest cavity to be drained.

With reference to the collection chamber 56, 58 and 60 (best shown in FIG. 3), the partitions 110, 112 divide the chamber into compartments 56, 58 and 60, to facilitate periodic monitoring of the level of liquid collected from the patient's cavity. As shown by arrows 104, 106 and 108 in FIG. 3, blood and other liquid 102 from the patient's chest cavity, via latex tube 96, drop into the compartment 56. When the compartment 56 is filled, the liquid will overflow into compartment 58 until that compartment is filled, whereupon additional liquid will overflow partition 112 and drop into compartment 60.

Compartment 56 is intentionally made to be relatively small compared, for example, to compartments 58 and 60. As a result, the quantity of liquid in compartment 56 may be more accurately determined. This feature is particularly useful in connection with the draining of liquids from pediatric patients where the quantity of liquid collected will be relatively small, and where relatively small amounts are medically significant.

As best shown in FIG. 4, the lower portion of rear wall 134 behind compartment 56 may be stepped, as at 122, 124, to render the bottom portion of compartment 56 of very small relative volume.

The underwater seal chamber, comprising compartments 62 and 64, is best shown in FIGS. 3, 5 and 7. The compartments 62 and 64 communicate with one another by virtue of the fact that the partition 132 terminates above the bottom wall 92 (see FIG. 5). Liquid (e.g., water 136; FIG. 3) is disposed in the bottom of the chamber and functions as a liquid seal to permit the flow of gases from the patient's chest cavity to atmosphere, but preventing reverse flow of gas. The flow path of gases suctioned from the patient's pleural cavity via latex tube 96 is shown by arrows 138, 140, 142, 144, 146 and 148 in FIGS. 3 and 5.

As best shown in FIG. 3, the upper end of the compartment 62 communicates with the collection chamber 56, 58, 60 through an opening 150 in a horizontal wall 152 which covers the upper end of compartment 62 of the underwater seal chamber and compartment 66 of the manometer chamber.

With reference to FIG. 5, the upper end of the other, larger compartment 64 of the underwater seal chamber 62, 64 communicates with the suction regulator 70.

The two compartments 66, 68 of the manometer chamber also communicate with one another at their bottoms since the partition 130 separating the compartments 66 and 68 terminates above the bottom wall 92, as best shown in FIG. 3. The upper end of the compartment 68 communicates with the atmosphere (see FIGS. 1, 2 and 3) and the upper end of the compartment 66 communicates with the collection chamber 56, 58, 60, through an opening 154 in the horizontal wall 152.

A quantity of liquid 156 is disposed in the bottom of the manometer chamber 66, 68 to indicate the negative pressure being applied to the patient's chest cavity; and a dye ball 158 is provided in the compartment 68 to color the liquid (e.g., water) disposed in chamber 66, 68 to facilitate reading of the pressure level via graduations 114 on the portion of the front wall 118 which overlies the compartment 66.

As illustrated in FIGS. 3, 5 and 22, a float valve 160 is provided at the upper end of compartment 62 of the underwater seal chamber 62, 64; and an identical float valve 161 is provided at the upper end of compartment 66 of the manometer chamber 66, 68. Both float valves 160 and 161 are provided for preventing the expulsion of the liquid 136 and 156, respectively, from their respective compartments 62 and 66.

As best shown in FIG. 22, the float valve 160 includes a generally cup-shaped valve member 162 which opens downwardly and is mounted on the bottom of a stem 163 which extends upwardly through the opening 150 and into a downwardly extending guide arm 164 in a guiding member 165. A sealing cup 166 is mounted on the top of valve member 162 for sealing the opening 150 when the liquid 136 in the compartment 62 rises and forces the valve member 162 upwardly.

It will thus be seen that when the liquid 136 rises to the top of compartment 62 of the underwater seal chamber 62, 64 (which rise would be created, for example, by a sudden increase in negativity in the patient's pleural cavity), it will carry the float valve 160 and sealing cup 166 upwardly to cover opening 150 and block fluid communication between compartment 62 and the collection chamber 56, 58, 60 to prevent the expulsion of the liquid seal 136.

The structure and function of float valve 161 at the top of compartment 66 of the manometer chamber 66, 68 is identical to the structure and operation of float valve 160 described above, and functions to block communication of the compartment 66 with the collection chambers 56, 58, 60 when high negativity in the patient's pleural cavity would otherwise suction the liquid 156 out of the compartment 66 through opening 154.

Suction is applied to the patient's pleural cavity, via the underwater seal chamber 62, 64 and the collection chamber 56, 58, 60 and the latex tube 96, by means of a suitable suction source (not shown); and the suction regulator 70 provides for convenient and accurate regulation of the level of suction applied to the patient.

The suction regulator 70, best illustrated in FIG. 16, includes a housing 170 which encloses a suction regulating chamber comprising an upper compartment 172 and a lower compartment 174 separated by a flexible diaphragm 176.

A downwardly projecting boss 180 on the bottom of the regulator housing 170 (FIG. 16) extends through a fitting 182 which, in turn, extends through an opening 184 in the top wall 76 of the casing 52 above the compartment 64 of the underwater seal chamber 62, 64. A sealing ring 245 is disposed between the boss 180 and the fitting 182 to provide a fluid tight connection therebetween.

A vertically movable nozzle member 190 is slidably disposed in a bushing 192 in the upper end of housing 170 and extends into the upper compartment 172 of the regulator chamber 172, 174. A reduced-diameter orifice 194 is provided in the forward end (or lower end, as viewed in FIG. 16) of the tube 190 in relatively close proximity to the diaphragm 176. The rear or upper end of the tube 190 is retained in a tubular adapter 196 which is externally threaded and received in an internally threaded boss 198 of a regulator control knob 200.

The regulator control knob 200 has an outer peripheral wall 202 which is internally threaded and fits over an upwardly extending, externally threaded boss 204 on the upper end of regulator housing 170.

This double-threaded arrangement (i.e., with mating threads on the fitting 196 and the interior boss 198 of knob 200, and the mating threads of peripheral wall 202 of knob 200 and the boss 204) permits vertical movement of the regulator tube 190 toward and away from diaphragm 176 by rotating the regulator control knob 200.

The upper end of fitting 196 is adapted to be received in the outer end of a tube 206 which is connected to a source of suction, now shown, such as a hospital suction supply.

The lower compartment 174 of the suction regulator chamber 172, 174 is open to atmosphere via a port 208 in the lower wall of the regulator housing 170.

The upper compartment 172 of regulator chamber 172, 174 is in fluid communication with the compartment 64 of the underwater seal chamber 62, 64 by means of passages 214, 216 which extend through the regulator housing 170, as shown on the left side of FIGS. 16 and 18.

Thus, when the chest drainage unit 50 is operating, suction from a suitable source (not shown) will, via tube 206, tubular stem 190, upper compartment 172, and passages 214 and 216, be applied to the compartment 64 of the underwater seal chamber 62, 64, as illustrated by the flow arrows in FIG. 16.

The degree of suction may be regulated by moving the reduced-diameter orifice 194 on the forward end of tubular stem 190 closer to or further from the diaphragm 176 by rotating the regulator adjustment knob 200 in a clockwise or counterclockwise direction.

When the suction (or negative pressure) being applied reaches a predetermined level, determined by the distance between orifice 194 and diaphragm 176, the central portion of the diaphragm will be sucked against orifice 194 to block off further suction. The central portion of the diaphragm 176 will remain in blocking engagement with the orifice 194 until the negativity in the collection chamber 56, 58, 60 and the patient's cavity being drained drops below the predetermined level (which will occur relatively quickly if air is leaking into the cavity).

When the degree of suction or negativity drops below the predetermined level, the elasticity of the diaphragm 176 will return the central portion of the diaphragm to its at-rest position, away from the orifice 194, to again establish communication between the suction source and the compartment 64 of the underwater seal chamber 62, 64.

The regulator housing 170 comprises two halves 171, 173, between which is sandwiched the outer periphery of the diaphragm 176. The upper and lower halves 171 and 173, respectively, of the housing 170 are secured to one another by any suitable means, such as screws 175 (FIG. 17), for example. A sealing ring 212 is provided between the passages 214, 216 which lead from the upper compartment 172 of the suction regulator chamber 172, 174 to the compartment 64 of the underwater seal chamber 62, 64.

The structure by which the suction regulator 70 is retained in the opening 184 in the top wall 76 of the casing 52 is best illustrated in FIGS. 9-16 and 19-21.

A fitting 182 (FIGS. 9, 10 and 20) is secured by any suitable means (e.g., adhesive) in the opening 184. The fitting 182 has a pair of circumferentially-spaced, radially-inwardly projecting, arcuate ledges 230, 232 on its inner peripheral wall adjacent the bottom thereof. The bottom portion of the counterclockwise-most end (as viewed from the top) of each of the ledges 230 and 232 are cut to form ramps 234 and 236, respectively (see FIGS. 10 and 11). A notch 238 is cut in the bottom, approximately central portion of the ledge 230 for receiving a cooperating detent 240 on one of the locking lugs 241 on the regulator 70.

Figure 14:
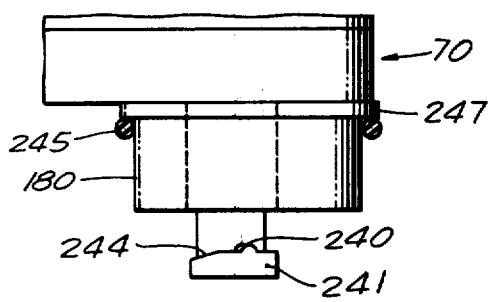
FIG. 14 is an elevation view from the vantage point of plane 14—14 of FIG. 13, looking in the direction of the arrows.
Figure 15:
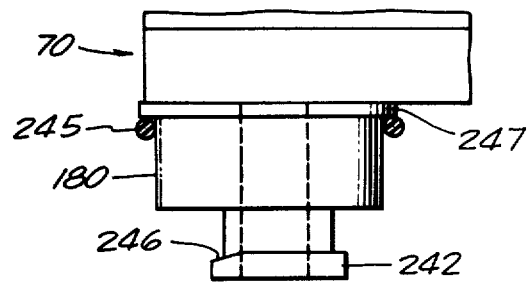
FIG. 15 is an elevation view from the vantage point of plane 15—15 of FIG. 13, looking in the direction of the arrows.

The locking lug 241 and a circumferentially-spaced, radially-outwardly projecting locking lug 242 are disposed on the bottom of a downwardly-extending cylindrical boss 180 on the bottom of the suction regulator 70. As best shown in FIGS. 14 and 15, the clockwise-most end (as viewed from above) of each of the locking lugs 241 and 242 are beveled on their top edges to provide ramps 244 and 246, respectively, which cooperate with the ramps 234 and 236 on ledges 230 and 232, respectively, to guide movement of the lugs 241 and 242 beneath the ledges 230 and 232, respectively, when the generally cylindrical boss 180 on the bottom of the regulator 70 is inserted into the fitting 182 and rotated in a clockwise direction.

It will be appreciated that the interlocking arrangement between the fitting 182 and the cylindrical boss 180 on the bottom of the regulator 70 is quite similar to the arrangement by which a radiator cap in an automobile fits on the opening into the radiator.

The locking detent 240 (FIGS. 14 and 21) on the locking lug 241 snaps into the identation 238 (FIG. 10) in the bottom of ledge 230 to lock the regulator 70 in place in the fitting 182 in the opening 184 in the top wall 76 of the casing 52.

A rubber O-ring 245 is provided around the generally cylindrical boss 180 beneath a circumferential ledge 247 thereon (FIGS. 13 and 16) to seal the connection between the generally cylindrical boss 180 and the fitting 182.

The vent valve-and-filter assembly 74, best illustrated in FIGS. 25-29, permits ready and convenient venting of the collection chamber 56, 58, 60 to filtered, atmospheric air. Such venting is necessary, for example, following a procedure called "milking" of the latex tube 96 between the patient and the unit 50. "Milking" is accomplished by squeezing the portion of the tube 96 adjacent the patient and running the fingers down along the tube toward the unit 50. When the tube is thereafter released, in the absence of venting of the collection chamber, a relatively high level of negativity will be reflected in the patient's pleural cavity causing the patient's tissue around the end of the catheter in the pleural cavity to be sucked into the holes, thereby causing irritation and damage. The vent valve-and-filter assembly 74 eliminates this potential hazard by permitting venting of the collection chamber by simply depressing a button.

Figure 25:
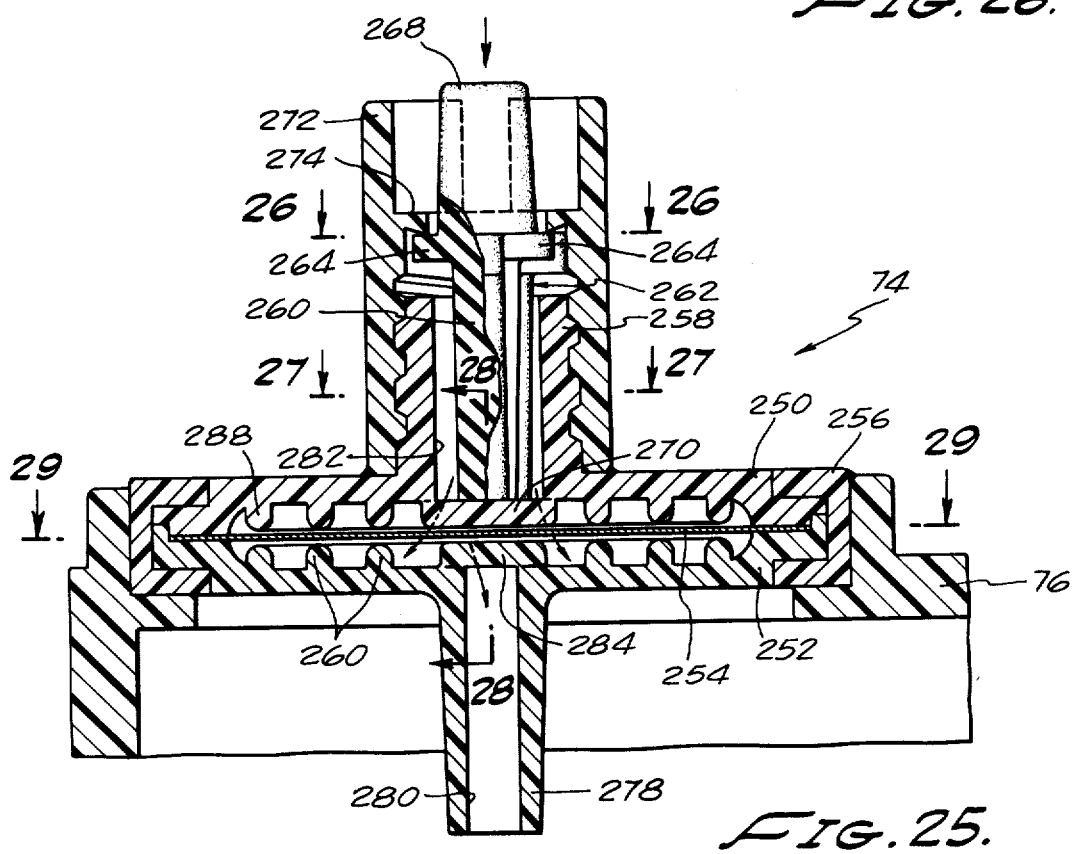
FIG. 25 is a sectional, front elevation view taken along the plane 25—25 of FIG. 2 and looking in the direction of the arrows, showing the manually-operable pressure relief valve/filter of the unit.

Referring to FIGS. 25-29 the vent valve-and-filter assembly 74 includes a two-part housing comprising an upper part 250 and a lower part 252, with bacterial filter paper 254 sandwiched therebetween. The two parts 250 and 252 and the filter paper 254 are held together in sandwiched relation, as shown in FIG. 25, by an annular clamping ring 256.

The upper part 250 of the housing 250, 252 includes an upwardly projecting, tubular, externally threaded boss 258 through which extends the stem portion 260 of a compressible, elastomeric valve member 262. The valve member 262 includes an annular flange 264 having a plurality of circumferentially-spaced, radially projecting protuberances 266 thereon (see FIG. 26). A pushbutton portion 268 extends upwardly above the flange 264.

Figure 27:
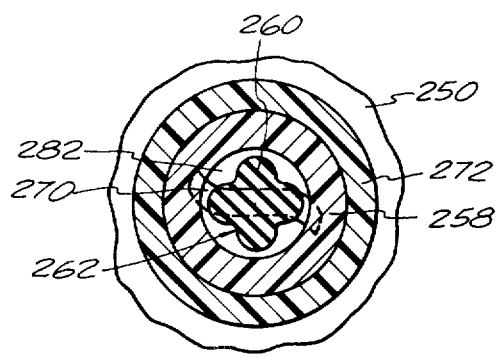
FIG. 27 is a sectional, top view taken along the plane 27—27 of FIG. 25 and looking in the direction of the arrows.
Figure 28:
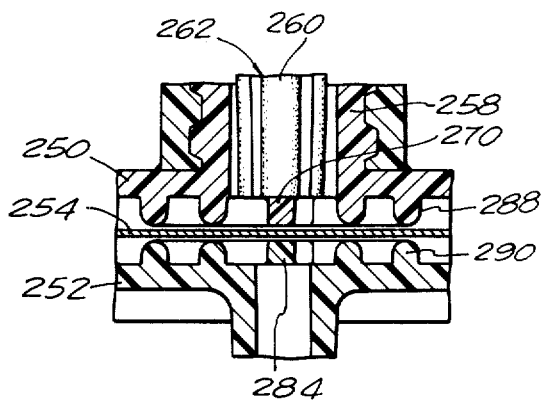
FIG. 28 is a sectional, front elevation view taken along the plane 28—28 of FIG. 25 and looking in the direction of the arrows.

The bottom of the stem portion 260 of the valve member 262 rests on a ledge 270 which extends across the central passage in the boss 258, as shown in FIGS. 25 and 27.

The valve member 262 is retained in position by means of a cap 272 having internal threads which cooperate with the external threads on the boss 258. A radially inwardly extending annular flange 274 on the cap 272 overlies the annular flange 264 on the valve 262 to retain the valve member 262 in place, as shown in FIG. 25.

The bottom portion 252 of the filter housing 250, 252 includes a downwardly extending tubular member 278 having a central tubular passage 280 which communicates, through filter paper 254, with the passages 282 between the stem 260 and the interior peripheral wall of boss 258 of the upper housing portion 250. A crosspiece 284 (FIGS. 25 and 29) extends across the passage 280.

Figure 29:
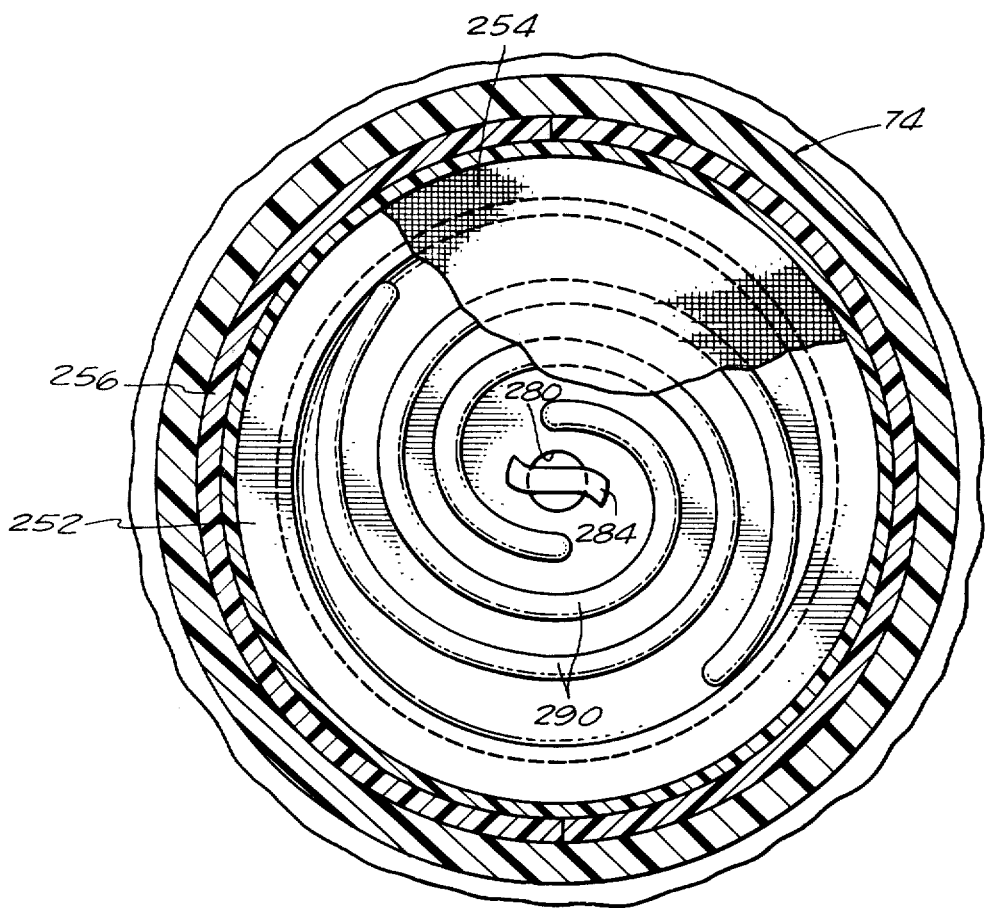
FIG. 29 is a sectional, top view taken along the plane 29—29 of FIG. 25 and looking in the direction of the arrows.

As best shown in FIGS. 25 and 29, spiral ridges 288, 290 are provided on the interior of the upper and lower housing portions 250 and 252, respectively, to provide support for the relatively thin bacterial filter paper 254.

When the button 268 of the elastomeric valve member 262 is depressed, the valve member will be compressed against the ledge 270 to permit atmospheric air to enter between the radially-inwardly extending ledge 274 of the cap 272 and the radially outwardly extending flange 264 on the valve member 262. Atmospheric air may then travel around the flange, through the annular spaces between the stem 260 and the boss 258, around the ledge 270, through the filter paper 254, around the crosspiece 284 and into the collection chamber 56, 58, 60.

Figure 23:
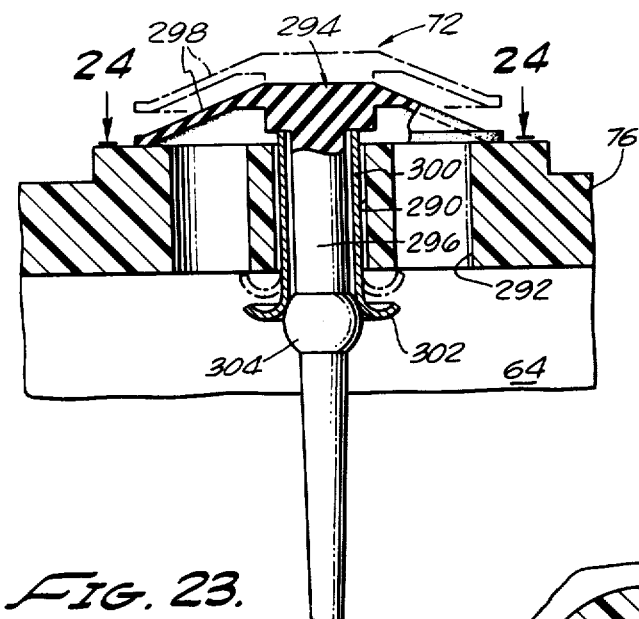
FIG. 23 is a sectional, front elevation view taken along the plane 23—23 of FIG. 9 and looking in the direction of the arrows illustrating the pop-off valve of the unit.
Figure 24:
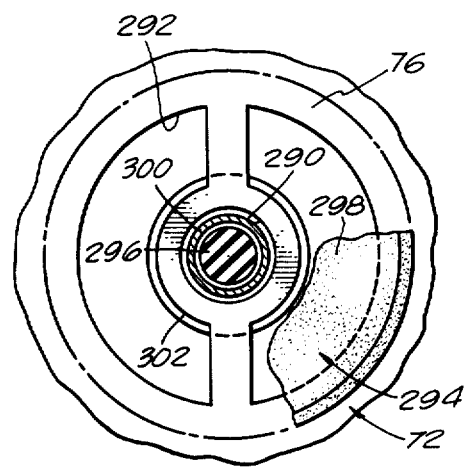
FIG. 24 is a sectional, top view taken along the plane 24—24 of FIG. 23 and looking in the direction of the arrows.
Figure 26:
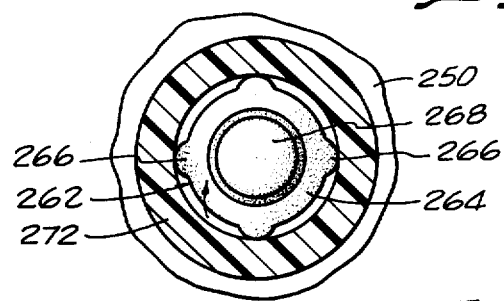
FIG. 26 is a sectional, top view taken along the plane 26—26 of FIG. 25 and looking in the direction of the arrows.

The pressure relief, pop-off valve assemmbly 72 is best illustrated in FIGS. 23 and 24. The top wall 76 of the casing 52 of the chest drainage unit 50 is provided with a central opening 290 and a concentric annular opening 292, located above the compartment 64 of the underwater seal chamber 62, 64. An "umbrella" valve member 294 has a central shaft portion 296 which extends through the central opening 290. The valve member 294 also includes a radially outwardly extending, annular flange 298 which overlies the annular opening 292.

A tubular sleeve 300 is disposed around the upper portion of the shaft 296 and includes an outwardly turned bottom end 302 which rests against an enlarged ball-shaped portion 304 in the central portion of the stem 296.

When positive pressure inside the compartment 64 of the underwater seal chamber 62 and 64 exceeds a predetermined "safe" level, the positive pressure felt by the annular flap 298 through the annular opening 292 will lift the flap, as shown in phantom lines in FIG. 23, to relieve the pressure. When the pressure in the compartment 64 returns to below the predetermined "safe" level, the flap 298 of the valve 292 will return it to the normal position, shown in solid lines in FIG. 23, again covering the openings 290 and 292.

OPERATION

In use, the outer end of the latex tube 96 is attached to a thoracic catheter (not shown) which, in turn, is inserted in the patient's chest cavity (e.g., pleural cavity) to be drained; and the other end of the tube 96 is attached to the casing 52 via the fitting 94. The tube 206 leading from the regulator 70 is connected to a suitable source of suction (not shown) such as a hospital suction source.

Water (or other liquid) 136 and 156 will previously have been poured into the bottom of the underwater seal chamber 62, 64 and the bottom of the safety seal/manometer chamber 66, 68. The water may be colored if desired to facilitate monitering of the drainage process.

The desired level of suction or negative pressure is set by rotating the control knob 200 on the suction regulator 70 to move the orifice 194 of the regulator nozzle 190 to a predetermined distance from the diaphragm 176 (FIG. 16).

Suction applied through the regulator 70 will be reflected through compartment 64 (FIG. 5), the liquid seal 136, compartment 62, collection chamber 56, 58, 60, thorocotomy tube 96 and the patient's cavity to be drained.

Liquid and gases sucked from the cavity will enter the casing 52 through the thorocotomy tube 96. The liquid (e.g., blood) will drop into chamber 56, and will overflow into compartments 58 and 60, as illustrated by arrows 106 and 108 (FIG. 3).

Gases suctioned from the cavity will travel across the upper portion of the collection chamber 56, 58, 60, as illustrated by arrows 138, 140 and 142 in FIG. 3, and will travel through the opening 150 in horizontal wall 152, down through the compartment 62, as illustrated by arrows 146 and 148 in FIG. 3, will bubble through the liquid seal 136, and pass up through the compartment 64, as shown in FIG. 5, and out through the suction regulator 70.

The liquid 156 in the safety seal manometer chamber 66, 68 will rise in the compartment 66 and fall in the compartment 68 when suction is applied, since the compartment 66 is in fluid communication with the underwater seal chamber 62, 64 and the suction regulator 70, via the openings 154 and 150 in the horizontal wall 152 (FIG. 3), to indicate the level of suction in the system.

In the event that the negativity in the collection chamber 56, 58, 60 rises to uch a level that it would otherwise suck the liquid 136 and 156 from compartment 62 and 66, the liquid will raise the float valves 160 and 161 to close off the openings 150 and 154 and prevent expulsion of the water therefrom.

If there occurs a positive pressure build up within the casing 52, the pop-off valve 294 of the assembly 72 (FIG. 23) will automatically pop up to relieve the pressure.

In the event that it is desired to vent the interior of the casing to filtered atmospheric air, the button 268 of the vent valve-and-filter assembly 74 is simply depressed.

From the foregoing it is apparent that the chest drainage unit 50 of the present invention is quiet in operation and is more compact and more economical than the prior art apparatuses described at the outset of the specification. The suction regulator 70 permits quiet operation inasmuch as it does not require the use of liquid to regulate the degree of suction applied to the cavity to be drained. Moreover, it is apparent that the suction regulator 70 provides for considerably more convenient setting of the desired suction level compared to the prior art. The suction level is set by simply rotating the control knob 200, instead of having to add or remove water, as is the case with the prior art systems.

The combination vent valveand-filter assembly provides for convenient venting of the collection chamber to filtered, atmospheric air.

It is contemplated, of course, that various modifications may be made to the particular embodiment illustrated in the drawings and described above without departing from the spirit and scope of the invention. Accordingly, it is intended that the scope of this patent be limited only by the scope of the following claims.

We claim:

1. In a chest drainage apparatus comprising a casing having a collection chamber therein for receiving fluid to be drained from a chest cavity, means defining an inlet opening into said collection chamber for establishing fluid communication between said collection chamber and a patient's chest cavity to be drained, means defining an outlet adapted to be connected in fluid communication with a source of suction, means defining a liquid seal between said collection chamber and said outlet, and a suction regulator for limiting the amount of suction applied to said collection chamber via said outlet and said liquid seal, the improvement comprising:

said suction regulator comprising:

a regulator housing defining a suction regulator chamber;

means defining an outlet opening from said regulator chamber which is in fluid communication with said collection chamber via said liquid seal;

means defining an inlet opening into said regulator chamber which is adapted to be connected to a source of suction;

pressure responsive means responsive to suction above a predetermined level in said collection chamber to block suction above about said predetermined level from said inlet opening chamber until the suction in said collection chamber drops to about said predetermined level;

said pressure responsive means comprising a flexible diaphragm in said regulator chamber;

a nozzle extending into said inlet opening in said regulator chamber; said nozzle including an outlet opening disposed adjacent one surface of said flexible diaphragm, whereby suction above said predetermined level at said one surface of said diaphragm in the vicinity of said nozzle will move a portion of said diaphragm against said nozzle outlet; and means for manually moving said nozzle toward and away from said flexible diaphragm so as to vary said predetermined level of suction at which said diaphragm in the vicinity of said nozzle will move against said nozzle outlet.

2. A chest drainage apparatus according to claim 1, and further comprising cooperating dog and ramp means on said regulator and on said casing for mounting said regulator on said casing with said regulator chamber disposed exterior of said casing.

* * * * *